United States Patent [19]

Eder et al.

[11] Patent Number: 4,808,922
[45] Date of Patent: Feb. 28, 1989

[54] MAGNETIC FIELD PRODUCING DEVICE FOR DETERMINING THE CONCENTRATION OF A PARAMAGNETIC SUBSTANCE PASSED THROUGH A ROTATING CELL CHAMBER

[75] Inventors: Alfred Eder, Wulfertshausen; Scato Albarda, Gross Schenkenberg, both of Fed. Rep. of Germany

[73] Assignee: Dragerwerk AG., Fed. Rep. of Germany

[21] Appl. No.: 944,257

[22] Filed: Dec. 18, 1986

[30] Foreign Application Priority Data

Dec. 19, 1985 [DE] Fed. Rep. of Germany ....... 3544967

[51] Int. Cl.[4] ...................... G01N 27/74; G01R 33/12
[52] U.S. Cl. .................................... 324/204; 73/27 A
[58] Field of Search ................ 324/204, 243; 73/27 A

[56] References Cited

U.S. PATENT DOCUMENTS

| 2,467,211 | 4/1949 | Hornfeck | 324/204 |
| 2,689,332 | 9/1954 | Greene | 73/27 A |
| 2,903,883 | 9/1959 | Luft | 73/27 A |
| 3,539,913 | 11/1970 | Prival | 324/204 |

FOREIGN PATENT DOCUMENTS 1924228 11/1970 Fed. Rep. of Germany.

Primary Examiner—Gerard R. Strecker
Attorney, Agent, or Firm—McGlew and Tuttle

[57] ABSTRACT

A device for the determination of the concentration of substances with paramagnetic properties, particularly oxygen, in substance mixtures comprises a cell assembly divided into several chambers, which is arranged to revolve with relation to a service for producing a magnetic field penetrating the cell assembly, and a coil assembly associated with this assembly for the conversion of the magnetic induction produced in it by the paramagnetic substance into an electrical signal. The assembly of devices producing magnetic fields and their associated measuring field coils is unaffected by external interferences such as transfer of mechanical vibrations or influences of external magnetic fields. For this purpose, at least four or more, even number of devices producing magnetic fields with their respective measuring field coils are arranged on both sides of the cell assembly and symmetrically to the axis of rotation, on a common housing, and the magnetizing polarity of the devices is combined with the magnetizing polarity of their respective measuring field coils in alternating orientation.

4 Claims, 2 Drawing Sheets

MAGNETIC FIELD PRODUCING DEVICE FOR DETERMINING THE CONCENTRATION OF A PARAMAGNETIC SUBSTANCE PASSED THROUGH A ROTATING CELL CHAMBER

FIELD AND BACKGROUND OF THE INVENTION

This invention relates in general to substance detection devices and in particular to a new and useful device for determining the concentration of a substance which has a paramagnetic property.

The invention particularly concerns a device for the determination of the concentration of substances with paramagnetic properties, particularly oxygen, in substance mixtures, comprising a cell assembly divided into several chambers, which revolve relative to a device for producing a magnetic field that penetrates the cell assembly, and a coil assembly associated with this device, which converts the magnetic induction produced in it by the paramagnetic substance into an electrical signal.

A similar device of this type is known from the German OS No. 1924228. The known device has a revolving cell assembly which is divided into several chambers and moves in the air gaps of two permanent magnets at a constant rpm. An electrical coil winding is attached about the yoke of each permanent magnet. In the presence of substances with paramagnetic properties in the measuring chambers of the cell assembly, the substance molecules within the magnetic fields produced by the permanent magnets orient themselves to varying degrees and induce an electrical signal in the coil assemblies, the intensity of which corresponds to the concentration of paramagnetic substances in the respective chamber of the cell assembly to be analyzed. The induced measuring signal is highly dependent on the magnetizing force produced by the permanent magnets. Every change or disturbance of this magnetic field results in a measurable and undesirable vitiation of the measuring signal. Interferences may occur, for example, when the air gaps of the magnet yokes are different in width. These gap widths may typically change during the measuring operation by not more than $10^{-8}$ mm, if a change in the measuring signal gap widths is to be less than 1% by volume $O_2$. External disturbing fields penetrate the cell assembly and vitiate the measuring result in an undesirable manner. An additional possible interference is the transfer of vibrations, e.g. due to the revolving cell assembly, or also due to shocks in the environment, to the permanent magnets, which stimulate these, together with the electrical signal coils, to start oscillatory motions, which alter the gap width of the permanent magnets and thereby produce a measuring signal in the signal coils (microphonic effect).

SUMMARY OF THE INVENTION

The present invention provides a device for the determination of the concentration of paramagnetic substances in such a way that the assembly of devices producing magnetic fields and their respective coil assemblies are unaffected by external interfering influence, e.g. transfer of mechanical vibrations or influences of an external magnetic field.

In accordance with the invention, at least four or a larger even number of devices producing magnetic fields with their respective measuring field coils on both sides of the cell assembly are arranged symmetrically to the rotational axis on a common housing, and the magnetizing polarity of the devices with the magnetizing polarity of their measuring field coils in alternate orientation to one another.

The significant advantage of the invention is seen in the fact that the alternating direction of the magnetizing polarity of devices producing magnetic fields, e.g. current carrying coils or permanent magnets, and their respective measuring field coils results in a compensation of interfering signal influences by stray fields or changes in the gap widths of the magnetic air gap due to mechanical vibrations. Vibrations of the top and bottom part of the housing, if they are regarded approximately at vibrations of the housing, are compensated to the third order and thus do not lead to a microphonic effect.

The devices producing magnetic fields are in the form of electrical coil bodies, which is particularly advantageous. The possibility of winding these together with the measuring field coils on a common core is then given. By synchronizing the points in time for the production of a magnetic field and for the measuring of the magnetic induction with the rpm of the cell assembly, the same substance mixture is determined at the same measuring time by two pairs of coils with different magnetizing polarities. Depending on the circuit connection, the compensation for the interference can be achieved for a two-chamber or a four-chamber cell.

When permanent magnets are used in the preferred manner for the production of the magnetic field within the chambers of the cell assembly, the variation in magnetizing polarity is obtained by the alternate arrangement of the north and south poles of the permanent magnets. The winding direction of the measuring coils alternates also in turn in this case.

Field conducting plates used to connect the coil cores cause an additional intensification when high frequency currents are applied to produce the magnetic fields.

Accordingly it is an object of the invention to provide a device for determining the concentration of a substance with a paramagnetic property particularly oxygen and particularly in substance mixtures which comprises a cell housing comprising a rotatable member having a plurality of cells with at least one containing control gas with at least one other having means for admitting a gas to be tested and which is rotatable in a housing which is provided with at least four or more even number of devices producing magnetic fields and including respective measuring field coils arranged on each side of the cell assembly and symmetrically to the axis of rotation and whereby magnetizing polarity of the respective measuring field coils and the magnetizing producing coils are arranged in alternating orientation.

A further object of the invention is to provide a device for determining the concentration of substances with paramagnetic properties which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
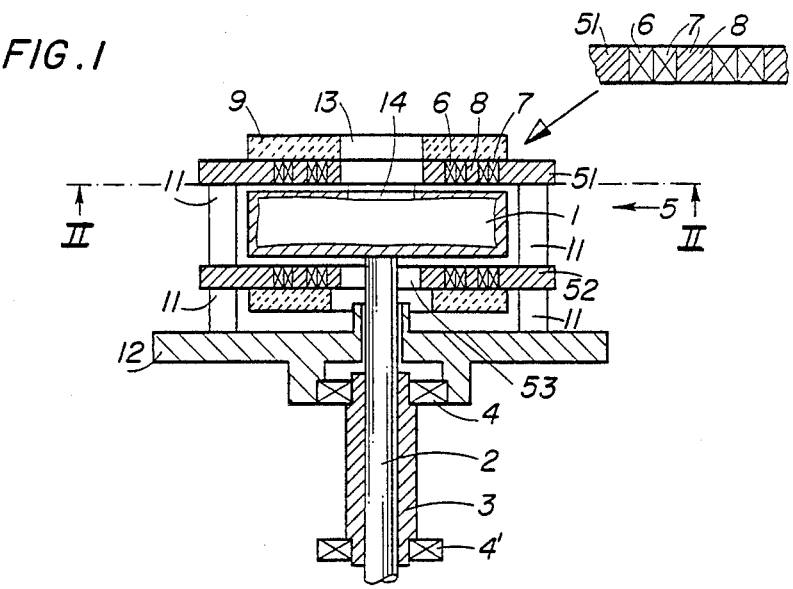
FIG. 1 is a sectional view of a cell assembly constructed in accordance with the invention with the respective magnetic field coils and measuring coils for determining the concentration of substances having paramagnetic properties.

Referring to the drawings in particular the invention embodied therein comprises a device for determining the concentration of substances with paramagnetic properties and particularly the presence of oxygen in substance mixtures which comprises a cell or an assembly of cells 1 which is mounted for rotation with a shaft 2 in a housing 5. In accordance with the invention, the housing 5 is provided with at least four devices or magnetic field coils that produce magnetic fields. These magnetic field coils and cooperating measuring field coils are arranged around the axis of the cell 1 symmetrically to the axis of rotation.

The magnetic field coils have a magnetizing polarity which is combined with the magnetizing polarity of the measuring field coils in alternate orientation to each other.

The device shown in FIG. 1 indicates a cell assembly 1, which is placed on a shaft 2 that is held in the rotary bearings 4,4' by a bushing 3. Cell 1 is driven by a motor that is not shown, which has its drive shaft connected to shaft 2. Shaft 2 passes through opening 53 of a bottom part of housing 5. Cell 1 is enclosed in housing 5. Coil assemblies include magnetic field coils 6 producing magnetic fields wound as a primary winding, and measuring field coils 7 wound as a secondary coil, around a common core 8 of ferrite ceramic. These coil assemblies are positioned on the housing top part 51 and bottom part 52, respectively. Four pairs, respectively 61, 62, 63, 64 of magnetic field coils 6 and measuring field coils 7 (coil assemblies) are provided on top part 51 and bottom part 52. Coils 6 are arranged to produce magnetic fields varying in polarization sign, which penetrates cell 1. Coil cores 8 are connected together by field conducting plates 9 of ferrite ceramic. Top part 51 and bottom part 52 rest on base plate 12, held by stays or upright members 11. The housing 5 and the field conducting plate 9 have intake openings 13 for the substance mixture to be tested, which can enter the measuring chambers of cell assembly 1 constructed in the known manner, through intake 14. The cell 1 is a four-chamber assembly, in which two measuring chambers with a flow of test substance mixture and two closed control chambers filled with a control substance are arranged in alternating sequence. After leaving the measuring chambers, the substance mixture leaves through respective radially arranged outlet openings in the cell side wall into atmosphere.

Figure 2:
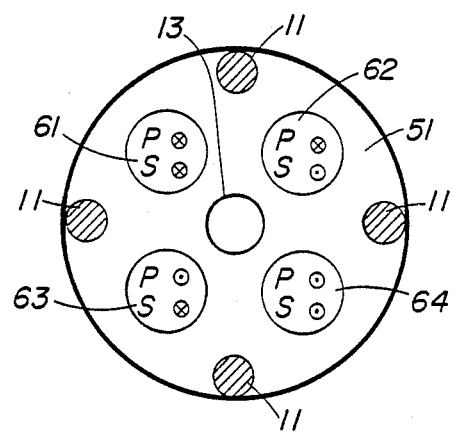
FIG. 2 is a bottom sectional view taken in the direction of line II—II of FIG. 1 of the arrangement of magnetic field coils and measuring coils with their respective winding direction.
Figure 3:
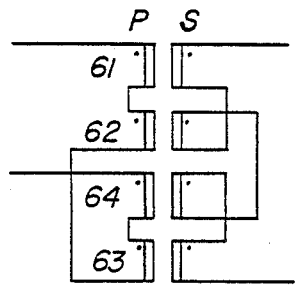
FIG. 3 is a diagram of the alternating winding direction of magnetic field and measuring coil.

FIG. 2 shows the view of the underside of top part 51, in which the assembly of four coil combinations 61, 62, 63, 64 is represented. The windings for the coils 6 producing magnetic fields are marked with P (primary winding) and the windings for the measuring field coils 7, with S (secondary coil). The sketched tilted crosses indicate the direction of the magnetic field into the plane of the drawing, the points within the circles indicate the direction of the magnetic field extending out of the plane of the drawing. The direction of the magnetic field of the individual coils 6,7 is explained in more detail by the diagram given in FIG. 3. The primary winding 6 and the secondary winding 7 of coil assemblies 61, 62, 63, 64 are marked with symbols. The point placed in the respective corners of the symbols indicates the winding direction of the repsecive coil assemblies 61, 62, 63 and 64.

Figure 4:
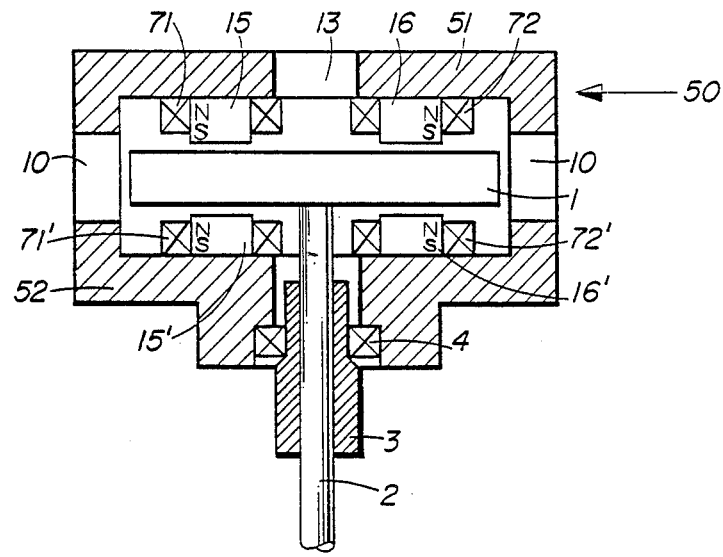
FIG. 4 is a sectional view similar to FIG. 1 of another embodiment of a cell assembly with permanent magnets and measuring coils.

FIG. 4 shows cell assembly 1 in a housing 50. Cell assembly 1 is also connected to rotary bearing 4 and an additional rotary bearing (not shown) through shaft 2 and bush 3. Top part 51 and bottom part 52 of housing 5 carry in the same arrangement as in FIG. 2 but with permanent magnets 15,16,17,18 and 15',16',17',18' instead of cores 8. The magnets are surrounded by measuring field coils 71,72,73,74, and 71',72',73', and 74', respectively. The closed housing 50 of magnetically soft material, which acts as magnetic screen, has an inlet opening 13 for the introduction of the substance mixture to be tested into cell assembly 1 and outlet slit 10 in radial position to cell assembly 1, through which the substance mixture leaving cell assembly 1 through the outlet openings can enter into the atmosphere.

Figure 5:
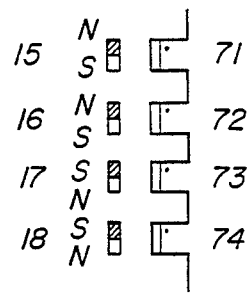
FIG. 5 is a schematic wiring diagram indicating the magnetic pole direction and the winding direction of the measuring coils.
Figure 6:
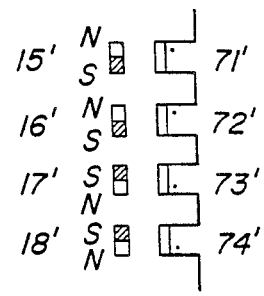
FIG. 6 is a schematic wiring diagram similar to FIG. 5 indicating the magnetic pole direction and winding direction of the measuring coils.

The assembly of permanent magnets 15,16,17,18 and their respective measuring field coils 71, 72, 73, 74 on top part 51 is schematically shown in FIG. 5. The assembly of permanent magnets 15', 16', 17' and 18' and their respective measuring field coils 71', 72', and 73' and 74' on bottom part 52 is schematically shown in FIG. 6. The north-south orientation of the permanent magnets 15,16,17,18 is coupled with the winding direction of measuring field coils 71,72,73,74 in such a way that a like magnet polarity corresponds with a like winding direction. The assembly of corresponding permanent magnets 15', 16', 17', 18' with their measuring field coils 71', 72', 73', 74' on the bottom part 52 is arranged in an analogous manner so that permanent magnets located opposite one another produce a magnetic field penetrating cell assembly 1.

While specific embodiments of the invention have been shown and described in detail to illustrate the application of the principles of the invention, it will be understood that the invention may be embodied otherwise without departing from such principles.

What is claimed is:

1. A device for determining the concentration of a substance with paramagnetic properties such as oxygen in a substance mixture comprising a body defining a hollow cell having an upper side and a lower side and having at least one control substance chamber and at least one measuring substance chamber through which a substance to be measured is passed, a housing, means in said housing for rotatably supporting said cell body for rotation therein, at least four devices each producing a magnetic field, and a plurality of measuring field coils each of said measuring field coils being associated with a corresponding one of said devices, respective pairs of said devices and corresponding measuring coils being arranged on both sides of said cell fixed to said housing and positioned symmetrically to the axis of said cell body axis of rotation, the magnetizing polarity of the devices being arranged with the magnetizing polarity of their respective measuring field coils in an alternating orientation.

2. A device according to claim 1, wherein said devices producing magnetic fields are in the form of electrical coil bodies, said coil bodies being wound together with a measuring field coil about a common core, by the alternating execution of the winding of the electrical coil body and the measuring field coil in the same direction and in an opposite direction.

3. A device according to claim 1, wherein the devices producing the magnetic coils are in the form of permanent magnets about which said measuring field coils are wound and have alternate winding directions, said permanent magnets being of the same polarity direction and combined with measuring field coils of the same winding direction.

4. A device according to claim 1, wherein said housing has a field conducting plate at its top and at its bottom containing said devices and said measuring field coils.

* * * * *